US011666743B2

(12) United States Patent
Werth et al.

(10) Patent No.: US 11,666,743 B2
(45) Date of Patent: Jun. 6, 2023

(54) VALVES

(71) Applicant: SAINT-GOBAIN PERFORMANCE PLASTICS CORPORATION, Solon, OH (US)

(72) Inventors: Albert A. Werth, Ft. Myers, FL (US); Clemens E. Zoellner, Bay City, MI (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 359 days.

(21) Appl. No.: 16/682,066

(22) Filed: Nov. 13, 2019

(65) Prior Publication Data

US 2020/0146934 A1 May 14, 2020

Related U.S. Application Data

(60) Provisional application No. 62/760,758, filed on Nov. 13, 2018.

(51) Int. Cl.
*A61M 39/22* (2006.01)
*F16K 5/04* (2006.01)
(Continued)

(52) U.S. Cl.
CPC ............ *A61M 39/22* (2013.01); *A61M 39/16* (2013.01); *F16K 5/0414* (2013.01);
(Continued)

(58) Field of Classification Search
CPC ...... A61M 39/22; A61M 39/16; A61M 39/02; A61M 39/0247; A61M 5/16881;
(Continued)

(56) References Cited

U.S. PATENT DOCUMENTS 2,673,570 A 3/1954 Cunningham et al.
3,465,778 A * 9/1969 Kast ..................... G05D 16/109
137/115.1
(Continued)

FOREIGN PATENT DOCUMENTS

CN 103498942 A 1/2014
CN 103968624 A 8/2014
(Continued)

OTHER PUBLICATIONS

International Search Report and Written Opinion for PCT/US2019/061085, dated Mar. 4, 2020, 12 pages.

*Primary Examiner* — Susan S Su
*Assistant Examiner* — Eric Rassavong
(74) *Attorney, Agent, or Firm* — Abel Schillinger, LLP; Chi Suk Kim

(57) ABSTRACT

A valve comprising: a valve body; and a valve stem disposed at least partially within the valve body, the valve stem comprising a sidewall defining a central lumen and at least one opening in the sidewall, wherein the valve is adapted to prevent fluid flow through the lumen when the at least one opening is disposed within the valve body and permit fluid flow through the lumen when the at least one opening is exposed from the valve body, and wherein the valve is essentially free of a spring.

19 Claims, 7 Drawing Sheets

(51) Int. Cl.
*A61M 39/16* (2006.01)
*A61M 39/24* (2006.01)

(52) U.S. Cl.
CPC ... *F16K 5/0442* (2013.01); *A61M 2039/2486* (2013.01); *A61M 2205/33* (2013.01)

(58) Field of Classification Search
CPC ....... A61M 2039/2486; A61M 2205/33; F16K 5/0414; F16K 5/0442; F16K 15/06; F16K 1/36; F16K 13/02
See application file for complete search history.

(56) References Cited

U.S. PATENT DOCUMENTS

| | | |
|---|---|---|
| 6,006,954 A | 12/1999 | Warby |
| 6,131,777 A | 10/2000 | Warby |
| 6,568,654 B1 | 5/2003 | Michna et al. |
| 7,997,458 B2 | 8/2011 | Wickham |
| 8,128,056 B2 | 3/2012 | Jung |
| 9,475,686 B2 | 10/2016 | Tuohey et al. |
| 10,415,718 B2 * | 9/2019 | Fatherazi .............. F16K 31/50 |
| 2006/0243942 A1 * | 11/2006 | Liepold .................. F16K 1/12 251/361 |
| 2007/0106264 A1 * | 5/2007 | Proulx .................. A61M 39/18 604/533 |
| 2009/0229671 A1 * | 9/2009 | Hartnett .............. A61M 39/22 137/13 |
| 2011/0052102 A1 | 3/2011 | Stiers et al. |
| 2011/0253233 A1 * | 10/2011 | Hillier .................. F16K 31/445 251/324 |
| 2015/0343195 A1 | 12/2015 | Laufer |
| 2017/0067568 A1 * | 3/2017 | Duncan .............. F16K 11/0853 |

FOREIGN PATENT DOCUMENTS

| | | |
|---|---|---|
| CN | 104379210 A | 2/2015 |
| JP | S5358328 U | 5/1978 |
| JP | S5511396 U | 1/1980 |
| JP | H0658431 A * | 3/1994 |
| KR | 20100027424 A | 3/2010 |
| WO | 2006088858 A2 | 8/2006 |
| WO | 2020102279 A1 | 5/2020 |

* cited by examiner

VALVES

CROSS-REFERENCE TO RELATED APPLICATION(S)

This application claims priority under 35 U.S.C. § 119(e) to U.S. Patent Application No. 62/760,758 entitled "VALVES," by Albert A. WERTH et al., filed Nov. 13, 2018, which is assigned to the current assignee hereof and incorporated herein by reference in its entirety.

FIELD OF THE DISCLOSURE

The present disclosure relates to valves.

RELATED ART

Valves can be utilized to restrict fluid flow between two or more fluid conduits. In particular, valves can be used in pharmaceutical and biological applications to permit selective restriction of fluid flow, such as for example when preparing pharmaceutical components.

The pharmaceutical and biological industries continue to demand improvements in valve design to minimize damage to fluid components and increase operational efficiencies and sterility.

BRIEF DESCRIPTION OF THE DRAWINGS

Embodiments are illustrated by way of example and are not intended to be limited in the accompanying figures.

DETAILED DESCRIPTION

Figure 1:
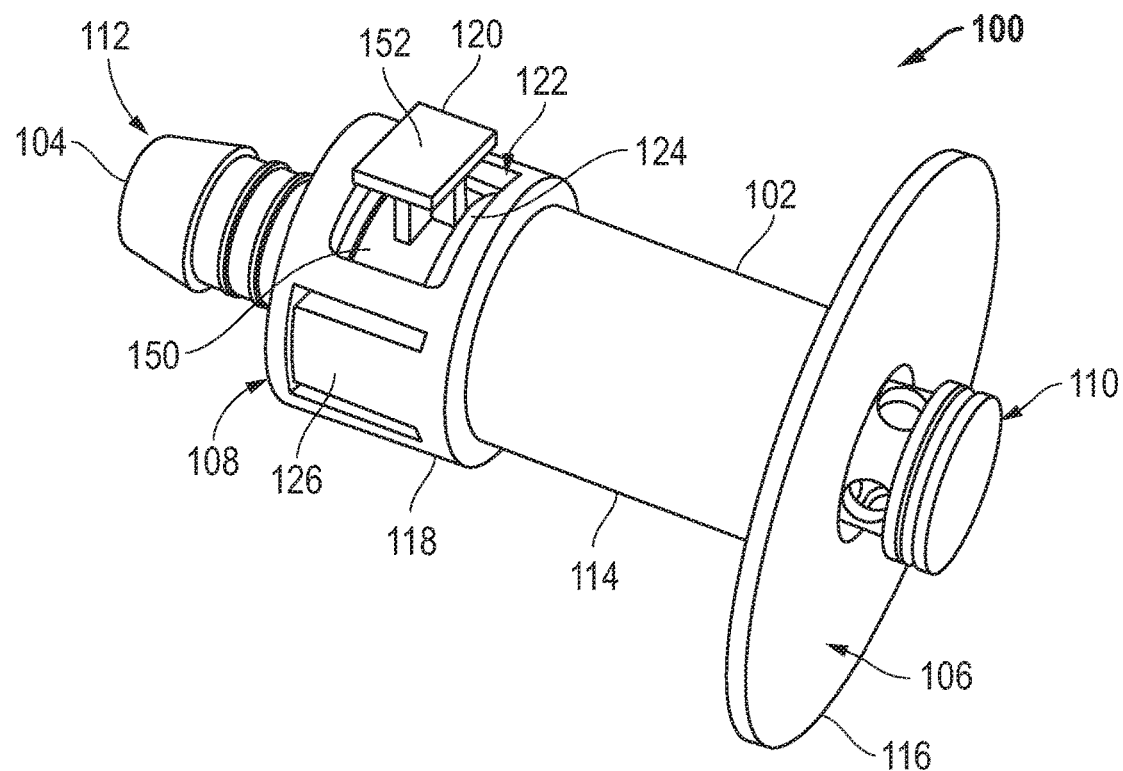
FIG. 1 includes a perspective view of a valve in accordance with an embodiment.

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

The terms "generally," "substantially," "approximately," and the like are intended to cover a range of deviations from the given value. In a particular embodiment, the terms "generally," "substantially," "approximately," and the like refer to deviations in either direction of the value within 10% of the value, within 9% of the value, within 8% of the value, within 7% of the value, within 6% of the value, within 5% of the value, within 4% of the value, within 3% of the value, within 2% of the value, or within 1% of the value.

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the valve and fluid transport arts.

In accordance with an aspect described herein, a valve can include a valve body and a valve stem disposed at least partially within the valve body. The valve stem can include a sidewall defining a central lumen and at least one opening in the sidewall. The valve can be adapted to prevent fluid flow through the lumen when the at least one opening is disposed within the valve body and permit fluid flow through the lumen when the at least one opening is exposed from the valve body. In a particular embodiment, the valve can be essentially free of a spring.

In accordance with another aspect described herein, a valve can include a valve body and a valve stem disposed at least partially within the valve body. The valve stem can be translatable between open and closed configurations. A retention feature can be adapted to selectively install relative to the valve stem. The retention feature can be adapted to selectively maintain the valve stem in the open configuration and the closed configuration.

In a particular instance, the valve can be adapted to selectively restrict fluid flow relative to a bag containing a biologically active composition or a pharmaceutical composition. In an embodiment, the valve stem can define a locking flange extending from the sidewall and adapted to engage with a retention feature to selectively maintain the valve stem in an open configuration and a closed configuration. In another embodiment, the valve stem can be translatable within the valve body upon application of an opening force, $F_O$, required to move the valve stem to the open configuration, or a closing force, $F_C$, required to move the valve stem to the closed configuration. In certain instances, $F_O$ and $F_C$ can be approximately equal when fluid pressures on both longitudinal ends of the valve stem are approximately equal.

In an embodiment, the valve body defines an axial length, as measured between first and second longitudinal ends thereof, less than an axial length of the valve stem, as measured between first and second longitudinal ends thereof. In another embodiment, the first longitudinal end of the valve stem is closed. In a more particular embodiment, the first longitudinal end of the valve stem can include a generally planar surface. The generally planar surface can extend along a plane generally perpendicular with a central axis of the lumen.

In certain instances the at least one opening can include a plurality of openings. In an embodiment, the planar surface disposed on the first longitudinal end of the valve stem can be tangent with the at least one opening.

In the open configuration, the at least one opening can be adapted to extend at least partially past the first longitudinal end of the valve body. In the closed configuration, the at least one opening can be adapted to be disposed between the first and second longitudinal ends of the valve body.

The valve can include a first seal disposed between the valve stem and the valve body at a location between the at least one opening and the second longitudinal end of the valve stem. The valve can further include a second seal disposed between the valve stem and the valve body at a location between the first longitudinal end of the valve stem and the at least one opening.

In certain instances, the valve can be installed in a fluid system between a first fluid conduit and a second fluid conduit. The first longitudinal end of the valve body can be disposed closer to the first fluid conduit. Fluid flow between the first and second fluid conduits can pass directly between the second fluid conduit and the lumen through an opening in the second longitudinal end of the valve stem and directly between the lumen and the first fluid conduit through the at least one opening.

In an embodiment, the valve stem can define a barbed interface adjacent to the second longitudinal end of the valve stem. The barbed interface can be adapted to receive a fluid conduit, such as one of the previously described fluid conduits. In a particular embodiment, the barbed interface can be adapted to receive a fluid hose.

FIG. 1 includes a perspective view of a valve 100 in accordance with an embodiment. The valve 100 can generally include a valve body 102 and a valve stem 104 disposed at least partially within the valve body 102. The valve stem 104 can be adapted to translate within an opening in the valve body 102 to move between open and closed configurations. In the open configuration, the valve 100 can permit fluid passage between two or more fluid conduits. In the closed configuration, the valve 100 can prevent fluid passage between two or more fluid conduits.

In an embodiment, the valve body 102 can have an axial length, $L_B$, as measured between a first longitudinal end 106 and a second longitudinal end 108, less than an axial length, $L_S$, of the valve stem 104, as measured between a first longitudinal end 110 and a second longitudinal end 112. For example, in a particular instance, $L_B$ can be no greater than 0.99 $L_S$, no greater than 0.98 $L_S$, no greater than 0.97 $L_S$, no greater than 0.96 $L_S$, no greater than 0.95 $L_S$, no greater than 0.9 $L_S$, or no greater than 0.85 $L_S$. In another instance, $L_B$ can be no less than 0.1 $L_S$, no less than 0.2 $L_S$, no less than 0.3 $L_S$, no less than 0.4 $L_S$, no less than 0.5 $L_S$, no less than 0.6 $L_S$, no less than 0.7 $L_S$, or no less than 0.8 $L_S$. In certain instances, the second longitudinal end 112 of the valve stem 104 can extend past the second longitudinal end 108 of the valve body 102 when the valve 100 is in the open and closed configurations.

Figure 4:
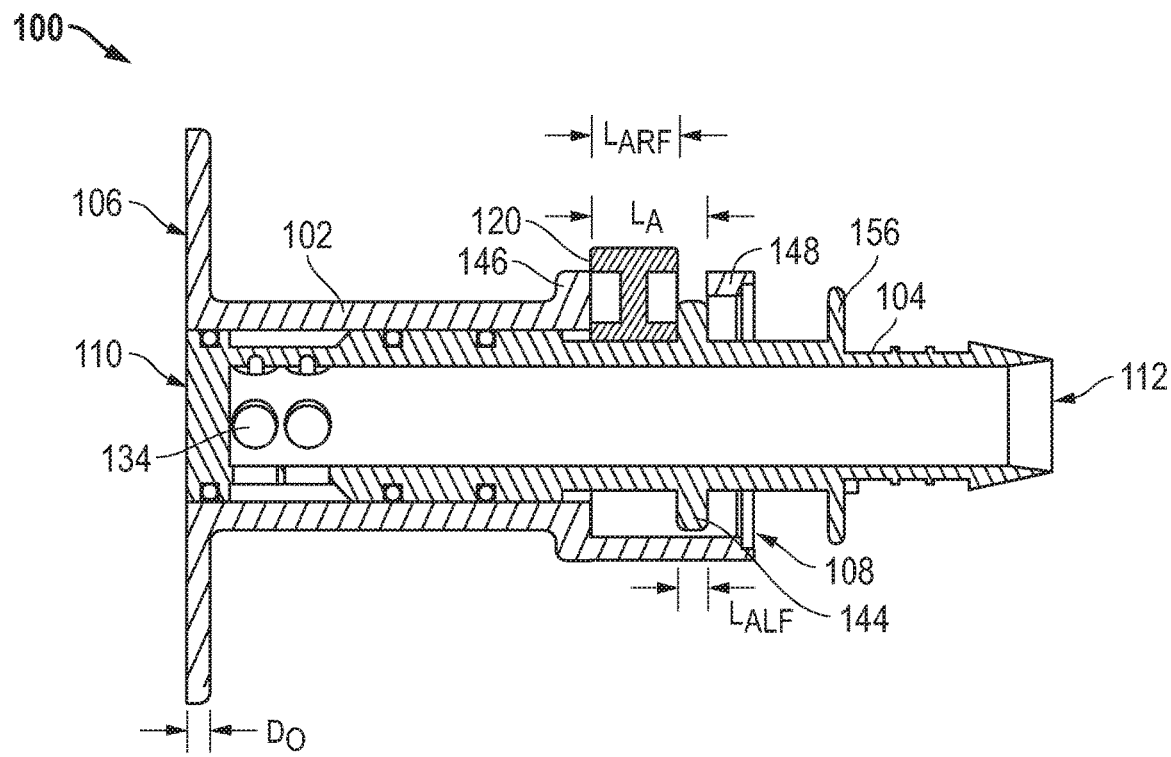
FIG. 4 includes a cross-sectional view of a valve in a closed configuration in accordance with an embodiment.
Figure 5:
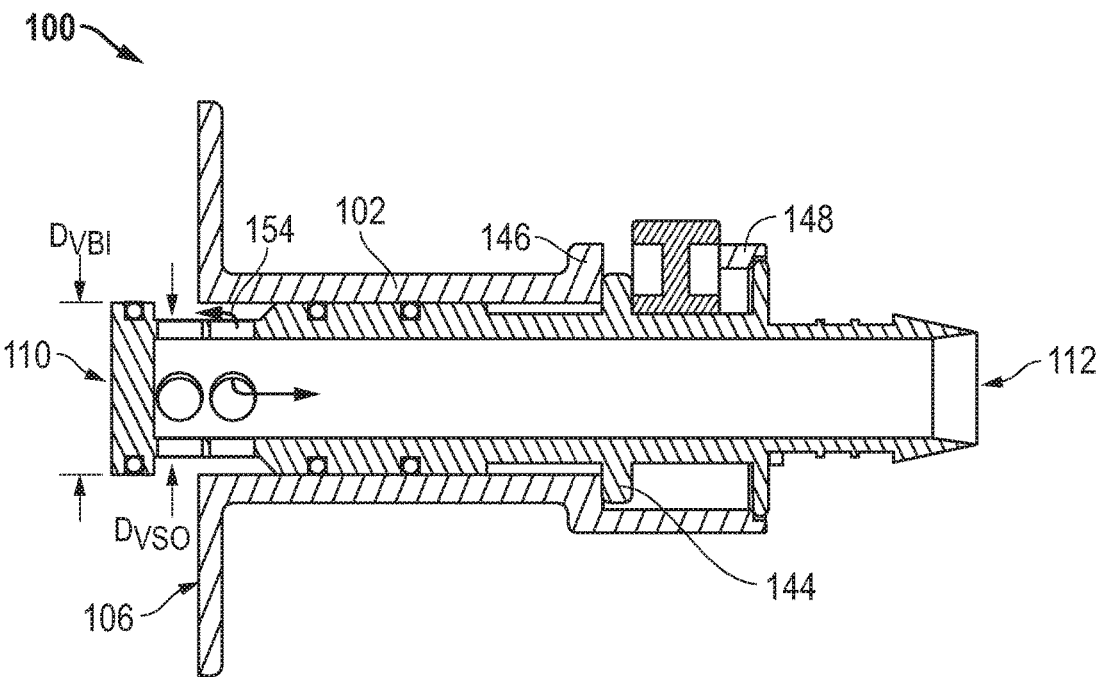
FIG. 5 includes a cross-sectional view of the valve stem in an open configuration in accordance with an embodiment.

In an embodiment, the valve 100 can be adjustable between a closed configuration (FIG. 4) and an open configuration (FIG. 5). In a particular embodiment, the valve 100 can be repeatedly adjustable between the open and closed configurations. In such a manner, an operator can selectively toggle the valve 100 between open and closed configurations. In another particular embodiment, the valve 100 can be adjustable between the open and closed configuration only once. That is, for example, the valve 100 can be adapted for single-use operations. By way of non-limiting example, the valve 100 can translate from the closed configuration to the open configuration and remain fixed in the open configuration. A stay, clip, or alternate one-time mechanism can prevent translation of the valve stem 104 after a single adjustment thereof. This may be particularly suitable for applications with single-use systems, such as with single use biopharmaceutical mixing bags. In certain instances, the valve 100 can include a single-use feature (not illustrated) adapted to retain the valve stem 104 in the open configuration after movement thereto.

Referring to FIG. 4, in an embodiment, the first longitudinal end 106 of the valve body 102 and the first longitudinal end 110 of the valve stem 104 can be disposed along a generally same plane when the valve 100 is in the closed configuration. In a more particular embodiment, the first longitudinal ends 106 and 110 can be disposed along a same plane when the valve 100 is in the closed configuration. The second longitudinal end 108 of the valve body 102 can be disposed between the first and second longitudinal ends 110 and 112 of the valve stem 104 when the valve 100 is in the closed configuration.

Referring to FIG. 5, in an embodiment, the first longitudinal end 106 of the valve body 102 can be disposed between the first and second longitudinal ends 110 and 112 of the valve stem 102 when the valve 100 is in the open configuration. The second longitudinal end 108 of the valve body 102 can be disposed between the first and second longitudinal ends 110 and 112 of the valve stem 104 when the valve 100 is in the open configuration.

Referring again to FIG. 1, the valve body 102 can include a cylindrical portion 114 coupled with a flange 116. In an embodiment, the flange 116 can be coupled with the cylindrical portion 114 at, or adjacent to, the first longitudinal end 106 of the valve body 102. The flange 116 can define a maximum diameter, $D_{MF}$, greater than a maximum diameter, $D_{MCP}$, of the cylindrical portion 114. For instance, $D_{MF}$ can be at least 1.01 $D_{MCP}$, at least 1.02 $D_{MCP}$, at least 1.03 $D_{MCP}$, at least 1.04 $D_{MCP}$, at least 1.05 $D_{MCP}$, at least 1.1 $D_{MCP}$, at least 1.2 $D_{MCP}$, or at least 1.3 $D_{MCP}$. In another embodiment, $D_{MF}$ can be no greater than 15 $D_{MCP}$, no greater than 12 $D_{MCP}$, no greater than 10 $D_{MCP}$, no greater than 7 $D_{MCP}$, no greater than 5 $D_{MCP}$, or no greater than 2 $D_{MCP}$. In a particular embodiment, the flange 116 can be adapted to be welded to a fluid conduit, such as a flexible bag or other fluid vessel. In a more particular embodiment, the flange 116 can be adapted to be sonically welded to the fluid conduit.

In an embodiment, the flange 114 can be generally planar. In a more particular embodiment, the flange 114 can be planar.

In certain instances, the cylindrical portion 114 of the valve body 102 can include an operational zone 118 wherein an operator can manipulate the valve 100, such as view the valve stem 104, adjust the valve stem 104, adjust a retention feature 120 adapted to selectively maintain the valve stem 104 at a desired configuration, or a combination thereof. In an embodiment, the operational zone 118 is spaced apart from the flange 116. In a more particular embodiment, the operational zone 118 can be disposed at, or adjacent to, the second longitudinal end 108 of the valve body 102.

The operational zone 118 of the valve body 102 can include one or more apertures 122 through which the valve stem 104 can be visible from an external environment. In an embodiment, the one or more apertures 122 can include a retention feature aperture 124 adapted to permit user engagement with the retention feature 120. In another embodiment, the one or more apertures 122 can include a clip feature 126 adapted to prevent undesired disengagement of the valve stem 104 from the valve body 102. The clip feature 126 can include, for instance, a portion of the valve body 102 having a lip or other retention feature adapted to prevent removal of the valve stem 104 from the valve body 102. During installation of the valve stem 104 with the valve body 102, the clip feature 126 can displace in a radial direction (e.g., radially outward) to permit passage of the valve stem 104 therethrough. After installation, the clip feature 126 can rebound toward the valve stem 104 and prevent undesired removal of the valve stem 104 from the valve body 102. In a particular instance, the valve 100 can include one clip feature 126. In other instances, the valve 100 can include a plurality of clip features 126, such as at least two clip features 126. The plurality of clip features 126 can be spaced apart from one another, such as in different apertures 122 within the operational zone 118 or within a same aperture 122.

In an embodiment, the retention feature aperture 124 can have a shape or size different from the aperture 122 containing the clip feature 126. In another embodiment, the retention feature aperture 124 and the aperture containing the clip feature 126 can have the same sizes or shapes as compared to one another. In a particular instance, the retention feature aperture 124 and the aperture 122 containing the clip feature 126 can be disposed along a same circumferential line extending around the circumference of the valve body 102.

In the illustrated embodiment, the operational zone 118 can have a greater radial height as compared to the remaining area of the cylindrical portion 114. In another embodiment, the operational zone 118 can be at a same radial height as the remaining area of the cylindrical portion 114. In yet another embodiment, the operational zone 118 can be at a lower radial height as compared to the remaining area of the cylindrical portion 114.

Figure 2:
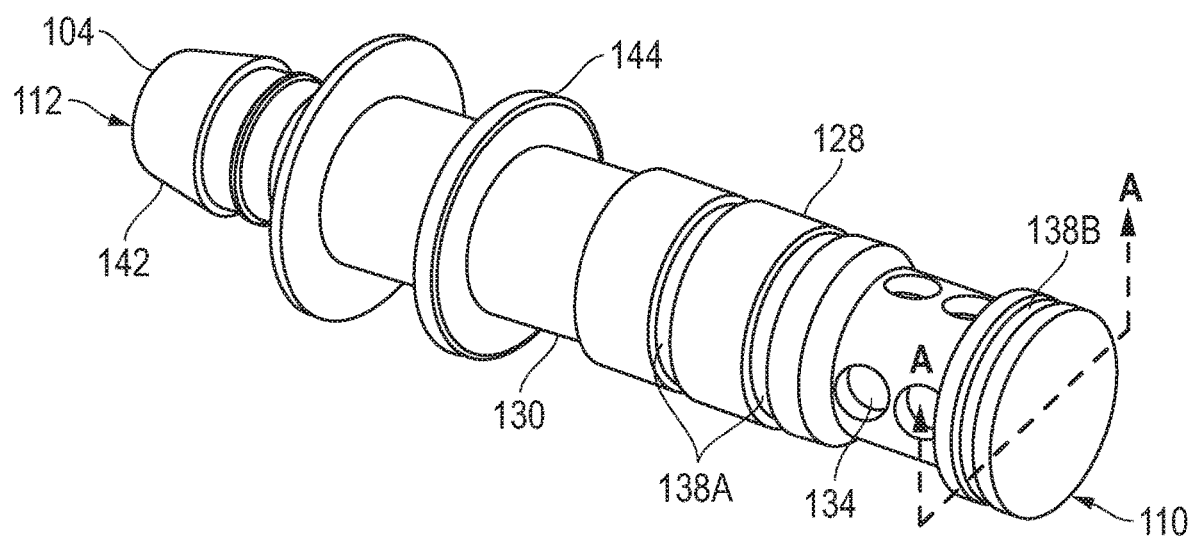
FIG. 2 includes a perspective view of a valve stem of the valve in accordance with an embodiment.

Referring to FIG. 2, the valve stem 104 can generally include a body 128 having a sidewall 130, such as a generally cylindrical sidewall. The sidewall 130 can define a central lumen 132 (FIG. 3) and at least one opening 134 extending through the sidewall 130. In an embodiment, the at least one opening 134 can extend from the external environment to the central lumen 132. That is, the central lumen 132 can be in fluid communication with the external environment through the at least one opening 134.

In an embodiment, the at least one opening 134 can include a plurality of openings, such as at least 2 openings, at least 3 openings, at least 4 openings, at least 5 openings, at least 6 openings, at least 7 openings, at least 8 openings, or at least 9 openings. In another embodiment, the at least one opening 134 can include no greater than 100 openings, no greater than 50 openings, or no greater than 20 openings. In an embodiment, at least two of the plurality of openings 134 can have a same size, a same shape, or both as compared to one another. In a more particular embodiment, all of the plurality of openings 134 can have a same size, a same shape, or both as compared to one another. In another embodiment, at least two of the plurality of openings 134 can have different sizes, different shapes, or both as compared to one another. In a more particular embodiment, all of the plurality of openings 134 can have different sizes, different shapes, or both as compared to one another.

The plurality of openings 134 can include openings disposed in columns, rows, or both. In an embodiment, the plurality of openings 134 can define at least two rows of openings extending around a circumference of the sidewall 130. In another embodiment, the plurality of openings 134 can define a first row of openings 134 and a second row of openings 134. In another embodiment, the plurality of openings 134 can define at least two columns of openings 134 disposed along lines generally parallel with a central axis of the valve 100.

Figure 3:
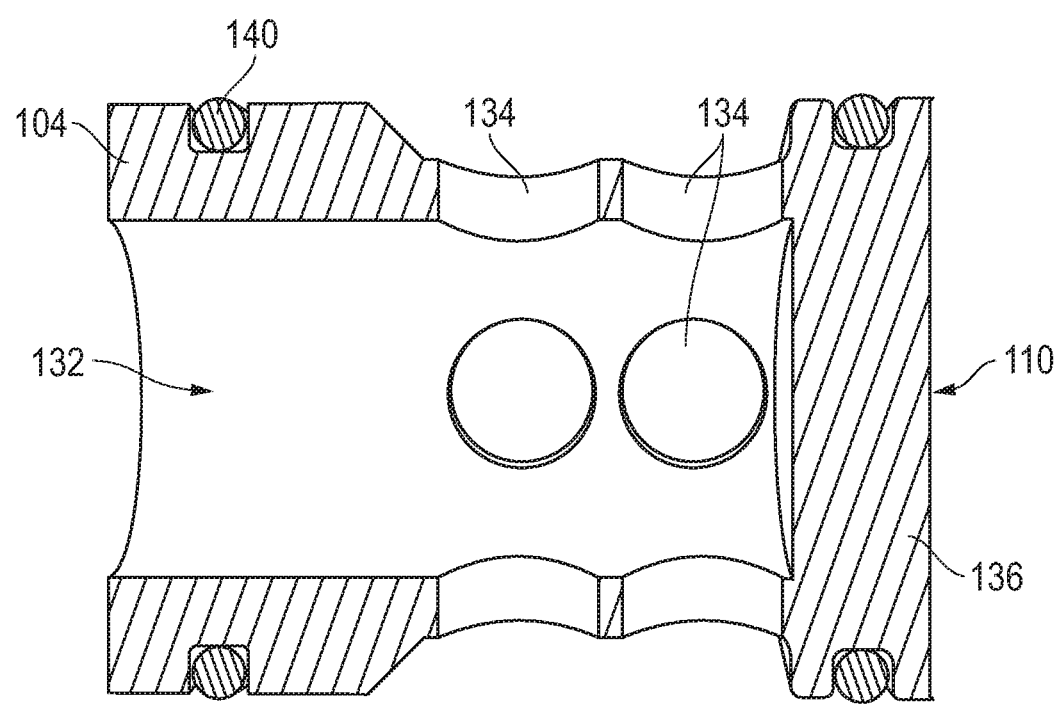
FIG. 3 includes a cross-sectional view of the valve stem in accordance with an embodiment as seen along line A-A in FIG. 2.

FIG. 3 illustrates a partial cross-sectional view of the valve stem 104 in accordance with an embodiment. The openings 134 illustrated in FIG. 3 are defined by round edges of the sidewall 130. More particularly, in the illustrated embodiment the openings 134 include circular cross-sectional shapes. In another embodiment, at least one of the openings 134 can have a non-circular shape, such as a polygonal shape. In a particular embodiment, at least one of the openings 134 can have a triangular shape, a quadrilateral shape, a pentagonal shape, a hexagonal shape, a heptagonal shape, an octagonal shape, a nonagonal shape, a decagonal shape, or another polygonal shape.

In an embodiment, the valve stem 104 can have a closed longitudinal end. In a more particular embodiment, the first longitudinal end 110 of the valve stem 104 can be closed. In such a manner, fluid can neither enter nor exit the central lumen 134 of the valve stem 104 through the longitudinal end 110 thereof. In an embodiment, the first longitudinal end 110 of the valve stem 104 includes a cap 136. The cap 136 can have a generally planar surface. The cap 136 can close the lumen 132 at the first longitudinal end 110. In an embodiment, the cap 136 can be integral with the sidewall 130 of the valve stem 104. For instance, the cap 136 can be monolithic with the sidewall 130. In another embodiment, the cap 136 can include a discrete element coupled with the sidewall 130.

In an embodiment, the one or more openings 134 can be spaced apart from the longitudinal end of the valve stem 104. In another embodiment, an inner surface of the cap 136 can be tangent with at least one of the one or more openings 134. That is, for example, a location of the at least one of the one or more openings 134 nearest to the cap 136 can be tangent with a generally planar surface of the cap 136.

Referring again to FIG. 2, in an embodiment, the valve stem 104 can define a plurality of grooves 138 each adapted to receive one or more seals 140 (FIG. 3). In an embodiment, the grooves 138 can be adapted to receive O-rings extending around a circumference of the valve stem 104. In a more particular embodiment, the seals 140 can sit within the grooves 138 and extend past an outer surface of the valve stem 104 such that they can sealingly engage with an inner surface of the valve body 102. In an embodiment, the grooves 138 can have a depth, $D_G$, as measured from a surface of the valve stem 104, less than a diameter, $D_S$, of the seals 140 adapted to be seated within the groove 138.

In an embodiment, the valve 100 can include a first groove location 138A disposed between the at least one opening 134 and the second longitudinal end 112 of the valve stem 104. In a particular embodiment, the first groove location 138A can include at least one groove 138, at least two grooves 138, at least three grooves 138, or at least four grooves 138. In another embodiment, the valve 100 can include a second groove location 138B disposed between the first longitudinal end 110 of the valve stem 104 and the at least one opening 134. Each groove 138 can be adapted to receive at least one seal 140, such as at least two seals, at least three seals, at least four seals, or at least five seals. In a particular embodiment, each groove 138 is adapted to receive one seal 140.

In a particular instance, the valve stem 104 can include two grooves 138 at the first groove location 138A and one groove 138 at the second groove location 138B. In an embodiment, at least one seal 140 disposed at the first groove location 138A can have a same shape, size, material composition, or any combination thereof as compared to the seal 140 disposed at the second groove location 138B. In another embodiment, at least one seal 140 disposed at the first groove location 138A can have a different shape, size, material composition, or any combination thereof as compared to the seal 140 disposed at the second groove location 138B.

The seals 140 can prevent fluid flow between the valve stem 104 and the valve body 102 when the valve 100 is in both the open and closed configurations.

As illustrated in FIG. 2, in an embodiment, the valve stem 104 can include an interface 142 adapted to receive and engage with a fluid conduit (not illustrated). In an embodiment, the interface 142 can be disposed at or adjacent to the second longitudinal end 112 of the valve stem 104. In an embodiment, the interface 142 can be adapted to form an interference fit with the fluid conduit. In a more particular embodiment, the interface 142 can include a barbed interface adapted to receive and engage the fluid conduit. In another embodiment, the interface 142 can include a bayonet connection, a threaded engagement interface, a clip or tab interface, another fluid conduit interface, or any combination thereof.

In an embodiment, the valve stem 104 can define a locking flange 144 extending from the sidewall 130. The locking flange 144 can be adapted to engage with the retention feature 120, the valve stem 104, or both in order to selectively maintain the valve 100 in the open and closed configurations. In an embodiment, the locking flange 144 can be visible from an external location to the valve body 102 when the valve stem 104 is installed therewith. In a more particular embodiment, the locking flange 144 can be at least partially visible through the aperture 122 of the valve body 104. In certain instances, the locking flange 144 can be visible from the external location when the valve 100 is in the open and closed configurations.

In an embodiment, the clip feature 126 can be adapted to engage with a complementary locking flange 156 of the valve stem 104 to prevent the valve stem 104 from disengaging with the valve body 102. In certain instances, the clip feature 126 can be at least partially disposed between the locking flange 144 and the complementary locking flange 156. More particularly, in an embodiment, a lip (not illustrated) of the clip feature 126 can be disposed between the locking flange 144 and the complementary locking flange 156. In certain instances, the locking flange 144 and complementary locking flange 156 can prevent axial displacement of the valve stem 104 from the valve body 102 in both longitudinal directions.

FIG. 4 illustrates an embodiment of the valve 100 in the closed configuration. FIG. 5 illustrates an embodiment of the valve 100 in the open configuration. Referring initially to FIG. 4, the valve body 102 can define a first stop feature 146 and a second stop feature 148 spaced apart from one another. In an embodiment, the first and second stop features 146 and 148 can be spaced apart from one another by an adjustment length, $L_A$. The locking flange 144 can be translatable along the adjustment length, $L_A$. In certain instances, the locking flange 144 can be translatable a maximum distance along the adjustment length, $L_A$, minus an axial length, $L_{ALF}$, of the locking flange 144. In certain instances, the adjustment length, $L_A$, is no less than a shortest distance, $D_O$, between the first longitudinal end 110 of the valve stem and the at least one opening 134. For example, $L_A$ can be at least 1.01 $D_O$, at least 1.02 $D_O$, at least 1.03 $D_O$, at least 1.04 $D_O$, at least 1.05 $D_O$, at least 1.1 $D_O$, or at least 1.2 $D_O$. In another example, $L_A$ can be no greater than 20 $D_O$, no greater than 15 $D_O$, no greater than 10 $D_O$, no greater than 5 $D_O$, or no greater than 2 $D_O$.

In an embodiment, the locking flange 144 can be adapted to contact the first stop feature 146 when the valve 100 is in the open configuration and contact the second stop feature 148 when the valve 100 is in the closed configuration. The retention feature 120 can be installed between the first and second stop features 146 and 146 to retard movement of the retention feature 120 when the valve 100 is selectively in the open or closed configurations.

In an embodiment, the retention feature 120 can be adapted to contact the first stop feature 146 when the valve 100 is in the closed configuration and contact the second stop feature 148 when the valve 100 is in the open configuration.

The retention feature 120 can define an axial length, $L_{ARF}$. In an embodiment, the adjustment length, $L_{AL}$, is in a range between 0.95 $[L_{ARF}+L_{ALF}]$ and 3.0 $[L_{ARF}+L_{ALF}]$, in a range between 0.97 $[L_{ARF}+L_{ALF}]$ and 1.5 $[L_{ARF}+L_{ALF}]$, or in a range between 0.99 $[L_{ARF}+L_{ALF}]$ and 1.1 $[L_{ARF}+L_{ALF}]$. In a more particular embodiment, $L_{AL}$ can be approximately equal to 1.0 $[L_{ARF}+L_{ALF}]$. In such a manner, the retention feature 120 can fit closely between the locking flange 144 and the first or second stop feature 146 or 148.

FIG. 5 illustrates the valve 100 in the open configuration with the one or more openings 134 extending at least partially beyond the first longitudinal end 106 of the valve body 102. The retention feature 120 is disposed between the locking flange 144 and the second stop feature 148. In this position, fluid can pass from the second longitudinal end 112 of the valve stem 104, through the central lumen 132, and through the one or more openings 134. Alternatively, fluid can pass through the one or more openings 134, through the central lumen 132, and out of the second longitudinal end 112 of the valve stem 104.

In an embodiment, the retention feature 120 can be adapted to provide an indication to the operator when the retention feature 120 is properly seated relative to the valve stem 104, the valve body 102, or both. The indication can include, for example, a tactile indication, an audible indication, or both.

In an embodiment, the valve stem 104 can define an outer diameter, $D_{VSO}$, as measured at the at least one opening 134, less than an inner diameter, $D_{VBI}$, of the valve body 102, as measured at the at least one opening 134 when the valve 100 is in the open configuration. In an embodiment, $D_{VSO}$ can be at least 1.01 $D_{VBI}$, at least 1.02 $D_{VBI}$, at least 1.03 $D_{VBI}$, at least 1.04 $D_{VBI}$, at least 1.05 $D_{VBI}$, or at least 1.1 $D_{VBI}$. In another embodiment, $D_{VSO}$ can be no greater than 10 $D_{VBI}$, no greater than 5 $D_{VBI}$, or no greater than 2 $D_{VBI}$. In such a manner, fluid flow through the at least one opening 134 can pass between the valve body 102 and valve stem 104 as indicated by line 154 in FIG. 5.

The retention feature 120 can generally define a body adapted to be installed within the aperture 122 of the valve body 102. Referring again to FIG. 1, the retention feature 120 can include a clip portion 150 adapted to seat at least partially around the valve stem 104 and a grippable portion 152 extending from the clip portion 150 to permit user grip therewith. The retention feature 120 can be moved, such as selectively moved, between an engaged position with the valve 100 and a disengaged position with respect to the valve 100. In an embodiment, the retention feature 120 can be detachable from the valve body 102 or valve stem 104. For instance, the retention feature 120 can be spaced apart from the valve stem 104 and valve body 102 when in the disengaged position.

Figure 11:
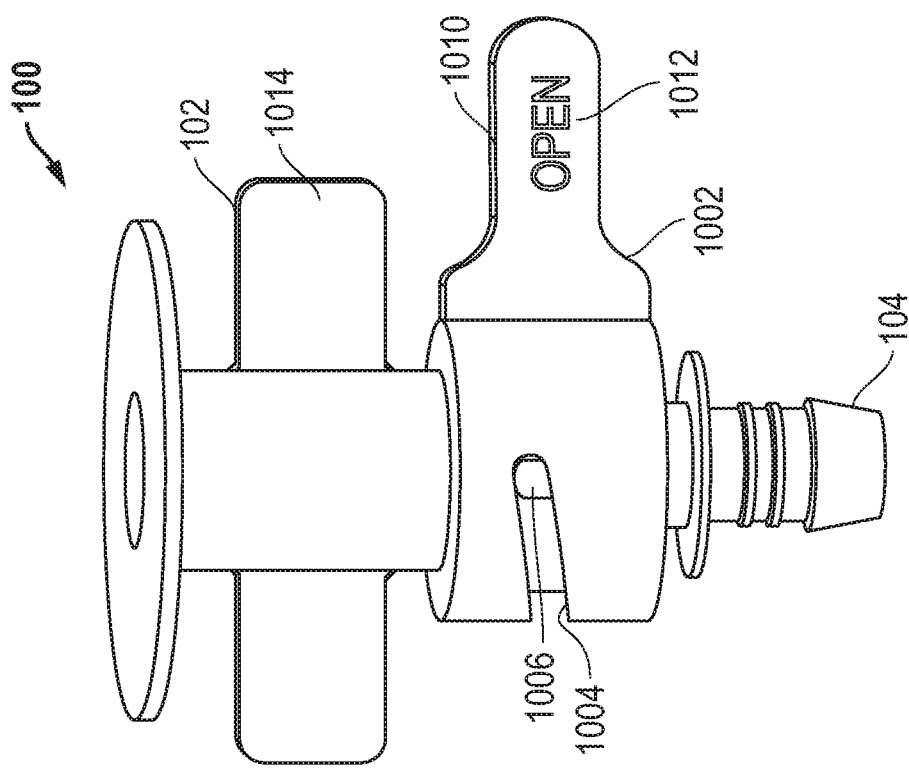
FIGS. 10 and 11 include perspective views of valves in accordance with embodiments.
Figure 10:
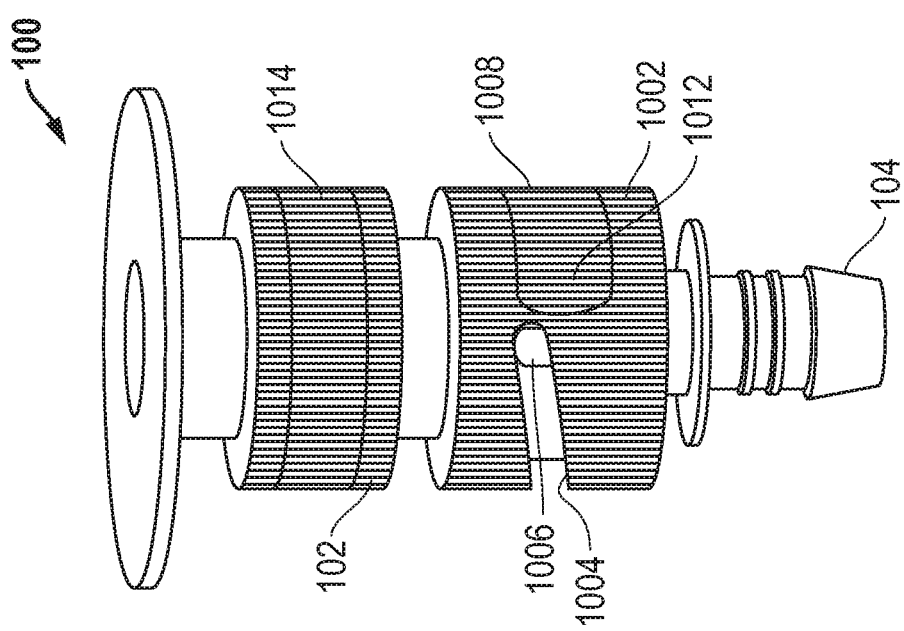

In another embodiment, the retention feature can be adapted to remain in contact with at least one of the valve stem 104 and valve body 102 when in the disengaged position. For instance referring to FIGS. 10 and 11, a retention feature 1002 can be rotatably coupled with the valve body 102 or valve stem 104. The valve stem 104 can translate relative to the valve body 102 upon rotatably biasing the retention feature 1002. Thus, for instance, the valve 100 can move between open and closed configurations upon rotational movement of the retention feature 1002.

As illustrated, the retention feature 1002 can include a ramp 1004. The ramp 1004 can extend around at least a portion of the circumference of the retention feature 1002, such as at least 10% of the circumference, at least 20% of the circumference, at least 30% of the circumference, at least 40% of the circumference, or at least 50% of the circumference. The ramp 1004 can define a ramp angle, as measured with respect to a plane perpendicular to an axis of the valve stem 104, of at least 1°, at least 2°, at least 3°, at least 4°, at least 5°, at least 10°, at least 15°, at least 20°, at least 25°, or at least 30°. In an embodiment, the ramp 1004 can include a cutout in the retention feature 1002. In a particular embodiment, the cutout can extend through a radial thickness of the retention feature 1002, such as through an entire radial thickness of the retention feature 1002.

In an embodiment, a portion 1006 of the valve stem 104 can extend through the valve body 102 to the retention feature 1002. The portion 1006 can engage with the ramp 1004 such that rotationally biasing the retention feature 1002 affects linear translation of the valve stem 104 relative to the valve body 102. In turn, the valve 100 can move between the open and closed configurations upon rotational movement imparted to the retention feature 1002. In an embodiment, the ramp 1004, portion 1006, or both can include tactile indications to the operator when the retention feature 1002 is transitioned an acceptable rotational distance. Further, the ramp 1004, portion 1006, or both can be adapted to maintain the retention feature 1002 in the desired configuration after completion of the rotational adjustment thereto.

In certain instances, the retention feature 1002 can include a grippable portion, such as a textured surface 1008 (FIG. 10), a tab or projection 1010 (FIG. 11), another grippable surface, or any combination thereof. The retention feature 1002 can include indicia 1012 to indicate directional operation of the retention feature 1002. For instance, the indicia 1012 can indicate which direction the retention feature 1002 is adjusted to open and close the valve 100. The indicia can include a color, a text or symbol, a surface characteristic, or another indicating element adapted to indicate to the operator how to adjust the valve 100. One or more complementary grippable elements 1014 can be included along the valve body 102 to facilitate easier rotational biasing of the retention feature 1002 relative to the valve body 102.

In a non-illustrated embodiment, the valve stem 104 can be translated manually (e.g., independent of the retention feature 1002) after the retention feature 1002 is rotated to a particular configuration adapted to permit translation of the valve stem 104. That is, for example, the retention feature 1002 does not have to impart translational movement to the valve stem 104 upon rotation of the retention feature 1002. In a particular embodiment, the retention feature 1002 can include a stop feature adapted to prevent translation of the valve stem 104 when the retention feature 1002 is in a first rotational position and permit translation of the valve stem 104 when the retention feature 1002 is in a second rotational position different than the first rotational position.

Figure 12:
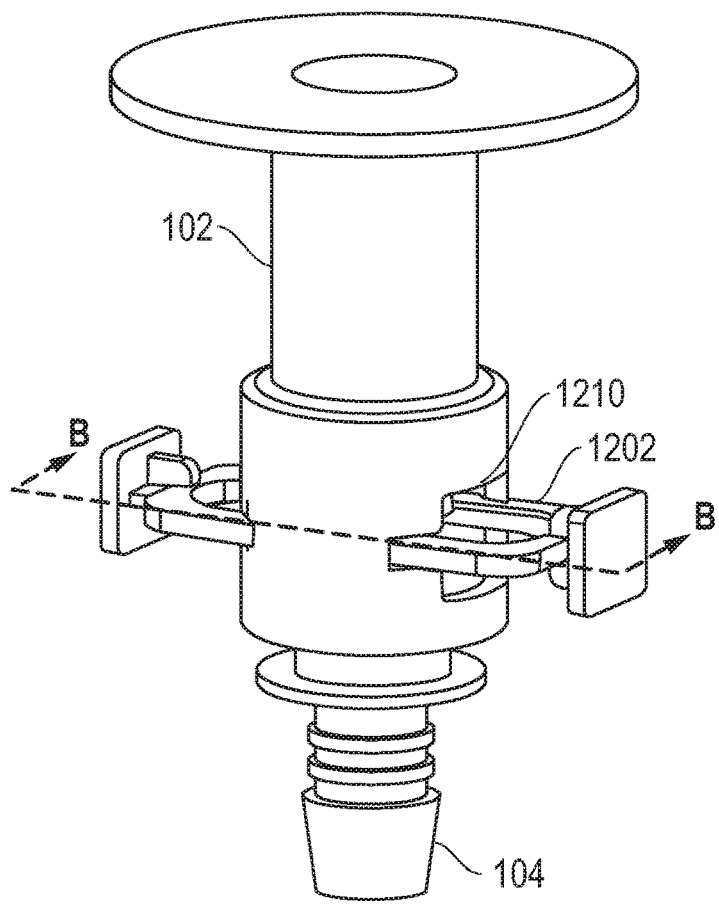
FIG. 12 includes a perspective view of a valve in accordance with an embodiment.
Figure 13:
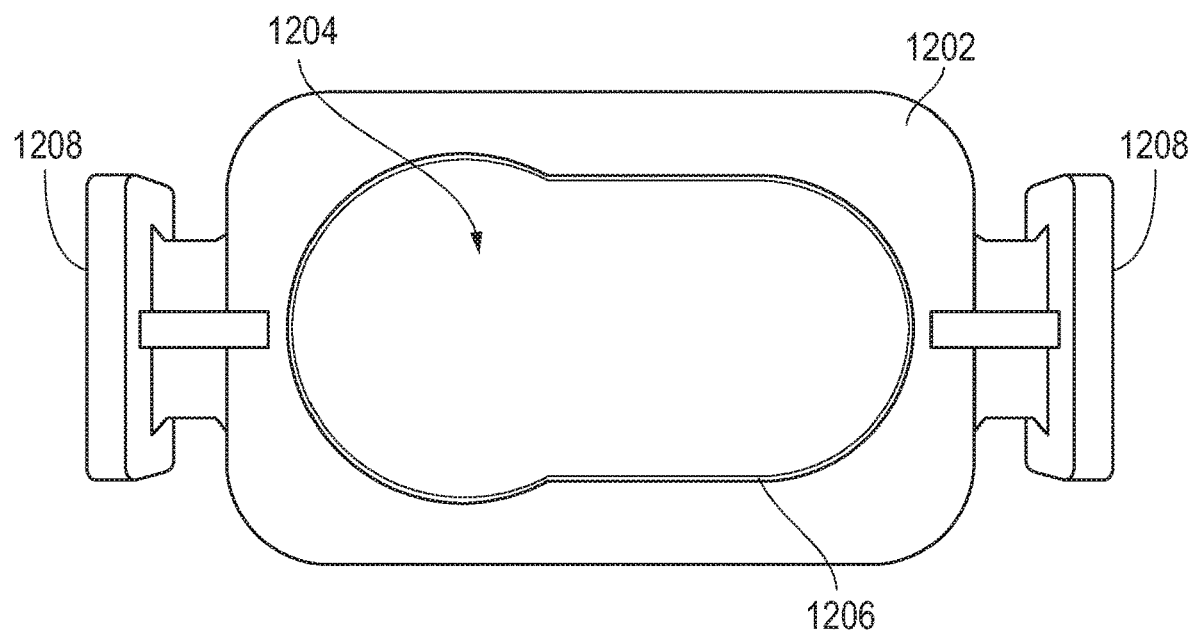
FIG. 13 includes a cross-sectional view of the valve of FIG. 12 in accordance with an embodiment, as seen along line B-B in FIG. 12.

FIGS. 12 and 13 illustrate another embodiment of a retention feature 1202 translatably coupled with the valve body 102 or valve stem 104. Referring to FIG. 13, the retention feature 1202 can include an adjustment zone 1204 and a lock zone 1206. The adjustment zone 1204 can correspond with an area of the retention feature 1202 adapted to permit adjustment of the valve stem between open and closed configurations. The lock zone 1206 can correspond with an area of the retention feature 1202 adapted to prevent adjustment of the valve stem between open and closed configurations.

In the illustrated embodiment, the retention feature 1202 can include one adjustment zone 1204 and one lock zone 1206. In another embodiment, the retention feature 1202 includes a plurality of lock zones 1206 and a single adjustment zone 1204. In a more particular embodiment, the adjustment zone 1204 can be disposed between lock zones 1206 and 1206. In another embodiment, the retention feature 1202 can include a plurality of adjustment zones 1204 and a single lock zone 1206 or a plurality of adjustment zones 1204 and a plurality of lock zones 1206. As illustrated, the adjustment zone 1204 can correspond with an area of the retention feature 1202 having a different dimension as compared to the lock zone 1206. For instance, the adjustment zone 1204 can include a dimension (such as a diameter) greater than a diameter of the lock zone 1206. In such a manner, the valve stem can translate relative to the retention feature 1202 when the valve stem is disposed within the adjustment zone 1204 and remain static relative to the valve body when the valve stem 104 is in the lock zone 1206.

Engageable portions 1208 can be disposed on the retention feature 1202 to permit operator access and adjustment thereof. In an embodiment, the engageable portions 1208 can be disposed on opposite sides of the retention feature 1202. In a particular embodiment, the engageable portions 1208 can be disposed on diametrically opposite sides of the retention feature 1202. In a more particular embodiment, engageable portions 1208 can be disposed along a line upon which the retention feature 1202 is adapted to translate during adjustment thereof. The engageable portions 1208 can include tabs, projections, textured surfaces, other grippable elements, or combinations thereof.

Referring to FIG. 12, the valve body 102 can include a cutout 1210 adapted to receive the retention feature 1202. In a particular embodiment, the cutout 1210 can be shaped to receive the engageable portions 1208 of the retention feature 1202.

In a non-illustrated embodiment, the retention feature 1202 can include a ramp adapted to translate the valve stem 104 in response to translation of the retention feature 1202. That is, for instance, translating the retention feature 1202 can affect translation of the valve stem 104 between open and closed configurations.

In certain instances, an opening force, $F_O$, required to translate the valve stem 104 to the open configuration is approximately equal to a closing force, $F_C$, required to move the valve stem 104 to the closed configuration. In a more particular embodiment, $F_O$ and $F_C$ can be approximately equal when fluid pressures on both longitudinal ends of the valve stem 104 are approximately equal. That is, in an embodiment, the valve 100 can be unbiased by a spring. More particularly, in an embodiment, the valve 100 can be essentially free of a spring or biasing means adapted to bias the valve stem 104, valve body 102, or both. Accordingly, moving the valve stem 104 can be performed with a generally same force in the opening and closing directions.

Figure 6:
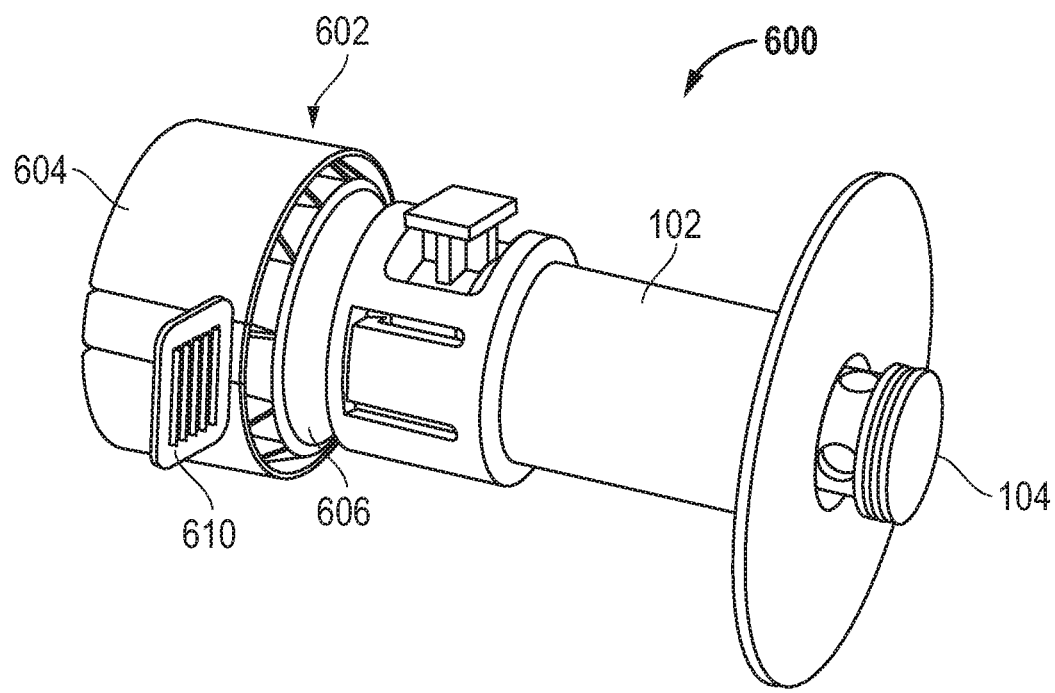
FIG. 6 includes a perspective view of a valve including a sanitary coupling in accordance with an embodiment.
Figure 7:
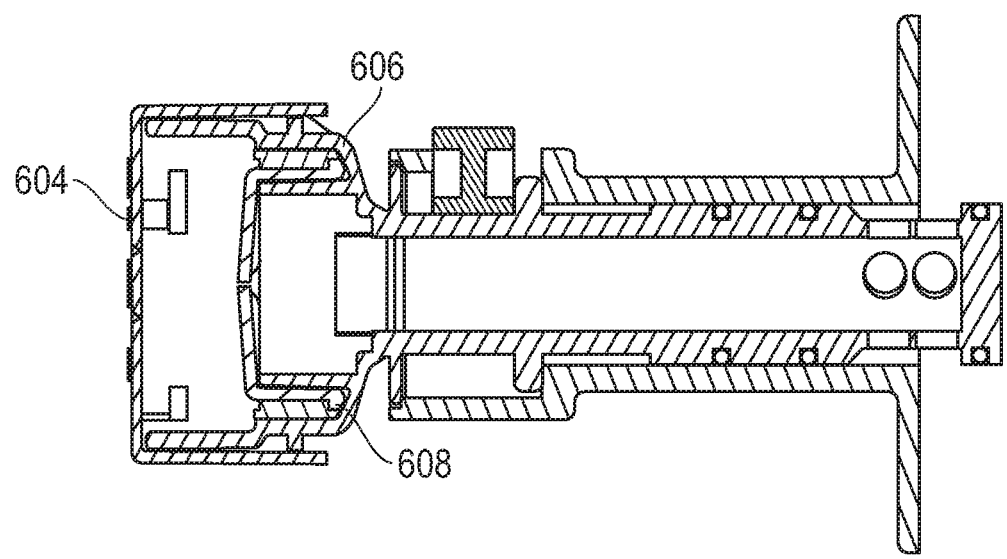
FIG. 7 includes a cross-sectional view of the valve of FIG. 6 in the open configuration in accordance with an embodiment.

In an embodiment, the valve can include a sanitary coupling. FIGS. 6 and 7 illustrate a valve 600 including a sanitary coupling 602. The valve 600 can include any number of similar or different features as described with respect to the valve 100. For instance, in an embodiment, the valve 600 can include a valve body 102 and a valve stem 104 disposed at least partially within the valve body 102.

The sanitary coupling 602 can cover exposed portions of the valve 600 which might come into contact with contaminant during operational usage. The sanitary coupling 602 can include a cover 604 adapted to secure with the valve body 102, the valve stem 104, or both. In an embodiment, the cover 604 can be coupled with the valve stem 104 at a location spaced apart from the valve body 102. In a more particular embodiment, the cover 604 can be coupled with only the valve stem 104 at a location spaced apart from the valve body 102. In an embodiment, the sanitary coupling 602 can include a portion of the valve stem 102 extending past the valve stem 102 previously described. For instance, instead of the interface 142 previously described, the valve stem 104 can terminate in an engagement interface 606 adapted to engage with the cover 604. A sanitary protector 608 can be disposed between the engagement interface 606 and the cover 604 to maintain a sterile valve 100 when not in use.

In certain instances, the cover 604 can include a grippable element 610 adapted to facilitate easier gripping and removal of the cover 604. The grippable element 610 can extend from the side of the cover 604 and project therefrom to permit user grip therewith. In certain instances, the cover 604 can include a single-use cover. In other instances, the cover 604 can be reused. In such embodiments, the grippable element 610 can facilitate easier installation of the cover 604 relative to the valve 600.

Figure 8:
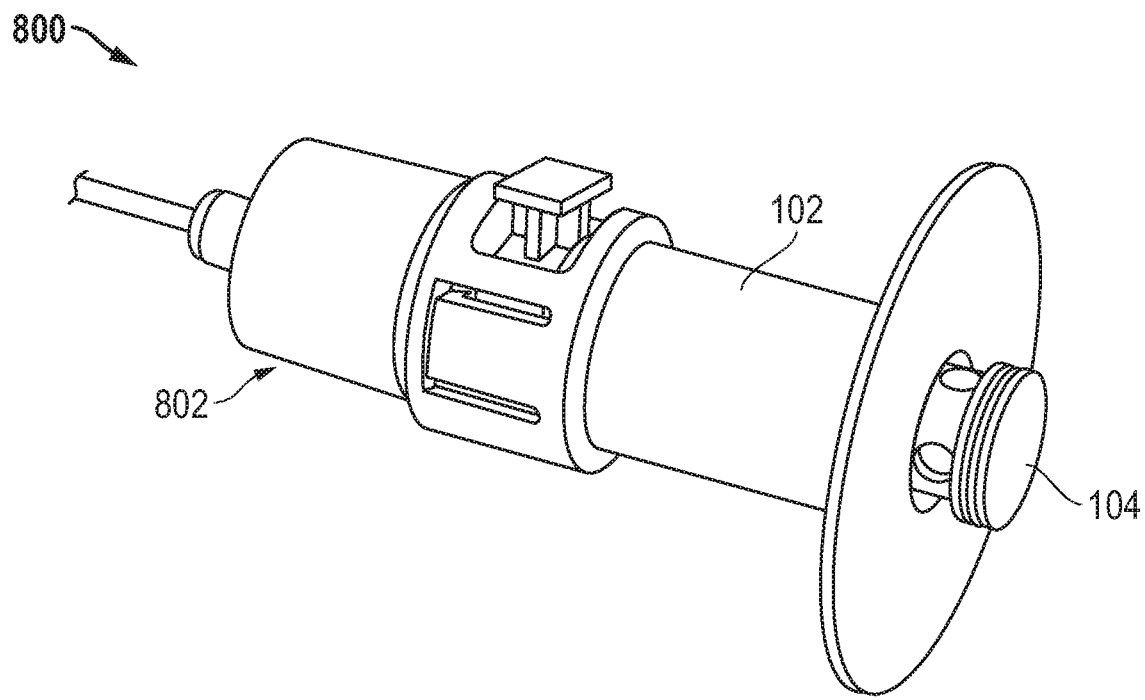
FIG. 8 includes a perspective view of a valve including a sensor in accordance with an embodiment.
Figure 9:
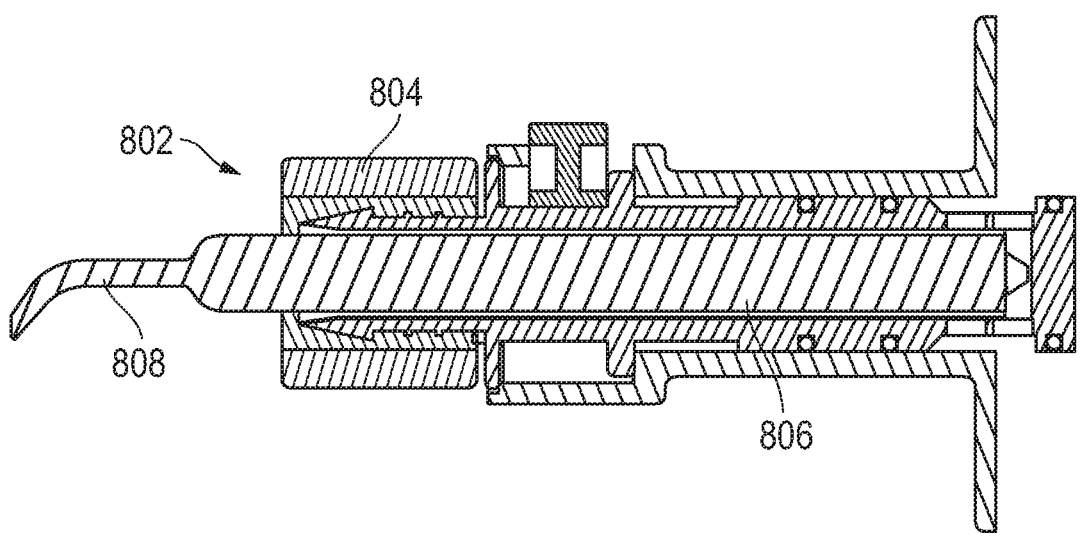
FIG. 9 includes a cross-sectional view of the valve of FIG. 8 in the open configuration in accordance with an embodiment.

FIGS. 8 and 9 illustrate a valve 800 including a sensor 802 adapted to sense a condition of the fluid within the fluid conduit coupled to the valve 800. In an embodiment, the valve 800 can include any number of similar or different features as described with respect to the valves 100 or 600. For instance, in an embodiment, the valve 800 can include a valve body 102 and a valve stem 104 disposed at least partially within the valve body 102. The valve stem 104 can be translatable within the valve body 102 to selectively contact the sensor 802 with fluid for purpose of measuring or detecting a condition of the fluid.

In the illustrated embodiment, the sensor 802 includes a housing 804 coupled with the valve stem 104 and a sensing element 806 disposed at least partially within the valve stem 104 and adapted to sense or detect a condition of the fluid. In certain instances, the sensing element 806 can be removable from the valve stem 104. In other instances, the sensing element 806 can be statically positioned relative to the valve stem 104.

The sensing element 806 can be in electrical communication with a logic device (not illustrated) including for instance, a microprocessor, through one or more wires 808. The one or more wires 808 can extend from the housing 804 and couple with the logic device.

The retention feature 120 can be selectively secured with the valve 800 to maintain the sensor 802 at a suitable position to sense or not sense the condition of the fluid.

Referring again to FIGS. 4 and 5, a method of operating the valve 100 in accordance with one or more embodiments described herein can generally include removing the retention feature 120 disposed between one of the first and second stop features 146 or 148 and the locking flange 144 of the valve stem 104. The method can further include translating the valve stem 104 in a direction generally parallel with respect to a longitudinal length of the valve stem 104. The method can additionally include installing the retention feature 120 between the other of the first and second stop features 146 or 148 and the locking flange 144.

In an embodiment, installing the retention feature 120 is performed such that the valve stem 104 remains at a fixed longitudinal position. Accordingly the valve 100 can be moved between the open and closed configurations and the retention feature 120 can selectively maintain the valve 100 in the desired configuration. Installation of the retention feature 120 can be performed by translating at least one of the retention feature 120 and valve stem 104 in a direction toward one another. Removal of the retention feature 120 can be performed by translating at least one of the retention feature 120 and valve stem 104 in a direction away from one another. In a particular embodiment, installation or removal of the retention feature 120 can be performed by translating the retention feature 120 perpendicular, or generally perpendicular, with the length of the valve stem 104.

In certain instances, removing the retention feature 120 can include disengaging the retention feature 120 from the valve stem 104 and the valve body 102. Removal of the retention feature 120 can include pulling the retention feature away from the valve stem 104.

In certain instances, the retention feature 120 can remain in contact with the valve 100 when disengaged therefrom. For instance, referring to FIGS. 10-13, the retention feature 1002 or 1202 can remain affixed to the valve 100 when the valve stem 104 is translated with respect to the valve body 102. In other instances, the retention feature 120 can be removed entirely from the valve 100 when disengaged therefrom.

Embodiment 1

A valve comprising:
a valve body; and
a valve stem disposed at least partially within the valve body, the valve stem comprising a sidewall defining a central lumen and at least one opening in the sidewall, wherein the valve is adapted to prevent fluid flow through the lumen when the at least one opening is disposed within the valve body and permit fluid flow through the lumen when the at least one opening is exposed from the valve body, and wherein the valve is essentially free of a spring.

Embodiment 2

A valve comprising:
a valve body;
a valve stem disposed at least partially within the valve body, wherein the valve stem is translatable between open and closed configurations; and
a retention feature adapted to be selectively installable relative to the valve stem, wherein the retention feature is adapted to selectively maintain the valve stem in the open and closed configurations.

Embodiment 3

The valve of any one of the preceding embodiments, wherein the valve is adapted to selectively restrict fluid flow relative to a bag containing a biologically active or pharmaceutical composition.

Embodiment 4

The valve of any one of the preceding embodiments, wherein the valve stem defines a locking flange extending from the sidewall, and wherein the locking flange is adapted to engage with a retention feature to selectively maintain the valve stem in an open and closed configuration.

Embodiment 5

The valve of embodiment 4, wherein the locking flange is visible from a location external to the valve body.

Embodiment 6

The valve of any one of embodiments 4 and 5, wherein the locking flange is at least partially visible through an aperture in the valve body.

Embodiment 7

The valve of embodiment 6, wherein the aperture extends around at least a portion of the circumference of the valve body.

Embodiment 8

The valve of any one of embodiments 4-7, wherein the locking flange is visible when installed relative to the valve stem in an open configuration and a closed configuration.

Embodiment 9

The valve of any one of embodiments 4-8, wherein the valve body defines a first stop feature and a second stop feature spaced apart by an adjustment length, and wherein the locking flange is translatable along the adjustment length.

Embodiment 10

The valve of embodiment 9, wherein the adjustment length, $L_A$, is no less than a shortest distance, $D_O$, between a first longitudinal end of the valve stem and the at least one opening.

Embodiment 11

The valve of embodiment 10, wherein $L_A$ is at least 1.01 $D_O$, at least 1.02 $D_O$, at least 1.03 $D_O$, at least 1.04 $D_O$, at least 1.05 $D_O$, at least 1.1 $D_O$, or at least 1.2 $D_O$.

Embodiment 12

The valve of any one of embodiments 10 and 11, wherein $L_A$ is no greater than 20 $D_O$, no greater than 15 $D_O$, no greater than 10 $D_O$, no greater than 5 $D_O$, or no greater than 2 $D_O$.

Embodiment 13

The valve of any one of embodiments 9-12, wherein the locking flange is adapted to contact the first stop feature when the valve is in the open configuration and contact the second stop feature when the valve is in the closed configuration.

Embodiment 14

The valve of any one of embodiments 9-13, wherein the retention feature is installable between the first and second stop features.

Embodiment 15

The valve of any one of embodiments 9-14, wherein the retention feature defines an axial length, $L_{ARF}$, wherein the locking flange defines an axial length, $L_{ALF}$, wherein the adjustment length defines a length, $L_{AL}$, and wherein $L_{AL}$ is in a range between 0.95 $[L_{ARF}+L_{ALF}]$ and 3.0$[L_{ARF}+L_{ALF}]$, in a range between 0.97 $[L_{ARF}+L_{ALF}]$ and 1.5 $[L_{ARF}+L_{ALF}]$, or in a range between 0.99 $[L_{ARF}+L_{ALF}]$ and 1.1 $[L_{ARF}+L_{ALF}]$.

Embodiment 16

The valve of embodiment 15, wherein $L_{AL}$ is approximately 1.0 $[L_{ARF}+L_{ALF}]$.

Embodiment 17

The valve of any one of embodiments 9-16, wherein retention feature is adapted to contact the second stop feature when the valve is in the open configuration and contact the first stop feature when the valve is in the closed configuration.

Embodiment 18

The valve of any one of embodiments 9-17, wherein the retention feature is moveable between an engaged position and a disengaged position.

Embodiment 19

The valve of embodiment 18, wherein the retention feature is adapted to remain in contact with at least one of the valve stem and valve body when in the disengaged position.

Embodiment 20

The valve of embodiment 18, wherein the retention feature is adapted to be spaced apart from the valve stem and valve body when in the disengaged position.

Embodiment 21

The valve of any one of the preceding embodiments, wherein the valve is essentially free of a spring.

Embodiment 22

The valve of any one of the preceding embodiments, wherein the valve stem is translatable within the valve body, and wherein an opening force, $F_O$, required to move the valve stem to an open configuration, is approximately equal to a closing force, $F_C$, required to move the valve stem to a closed configuration, as measured when fluid pressures on both longitudinal ends of the valve stem are approximately equal.

Embodiment 23

The valve of any one of the preceding embodiments, wherein the valve body defines an axial length, as measured between first and second longitudinal ends, less than an axial length of the valve stem, as measured between first and second longitudinal ends.

Embodiment 24

The valve of embodiment 23, wherein the first longitudinal ends of the valve body and valve stem are disposed along a generally same plane when the valve is in the closed configuration.

Embodiment 25

The valve of any one of embodiments 23 and 24, wherein the second longitudinal end of the valve body is disposed between the first and second longitudinal ends of the valve stem when the valve is in the closed configuration.

Embodiment 26

The valve of any one of embodiments 23-25, wherein the first longitudinal end of the valve body is disposed between the first and second longitudinal ends of the valve stem when the valve is in the open configuration.

Embodiment 27

The valve of any one of embodiments 23-26, wherein the second longitudinal end of the valve body is disposed between the first and second longitudinal ends of the valve stem when the valve is in the open configuration.

Embodiment 28

The valve of any one of the preceding embodiments, wherein a first longitudinal end of the central lumen of the valve stem is closed.

Embodiment 29

The valve of any one of the preceding embodiments, wherein the first longitudinal end of the valve stem comprises a generally planar surface.

Embodiment 30

The valve of any one of the preceding embodiments, wherein the at least one opening comprises a plurality of openings.

Embodiment 31

The valve of embodiment 30, wherein the plurality of openings define at least two rows of openings extending around a circumference of the sidewall.

Embodiment 32

The valve of any one of embodiments 30 and 31, wherein at least two of the plurality of openings have a same size, a same shape, or both.

Embodiment 33

The valve of any one of embodiments 30-32, wherein at least two of the plurality of openings have different sizes, different shapes, or both.

Embodiment 34

The valve of any one of the preceding embodiments, wherein a planar surface disposed on a first longitudinal end of the valve stem is tangent with the at least one opening.

Embodiment 35

The valve of any one of the preceding embodiments, wherein the at least one opening is adapted to extend at least partially past the first longitudinal end of the valve body when the valve is in the open configuration.

Embodiment 36

The valve of any one of the preceding embodiments, wherein the at least one opening is adapted to be disposed between the first and second longitudinal ends of the valve body when the valve is in the closed configuration.

Embodiment 37

The valve of any one of the preceding embodiments, wherein the valve stem defines an outer diameter, $D_{VSO}$, as measured at the at least one opening, less than an inner diameter, $D_{VBI}$, of the valve body, as measured at the at least one opening when the valve is in the open configuration.

Embodiment 38

The valve of embodiment 37, wherein $D_{VSO}$ is at least 1.01 $D_{VBI}$, at least 1.02 $D_{VBI}$, at least 1.03 $D_{VBI}$, at least 1.04 $D_{VBI}$, at least 1.05 $D_{VBI}$, or at least 1.1 $D_{VBI}$.

Embodiment 39

The valve of any one of embodiments 37 and 38, wherein $D_{VSO}$ is no greater than 10 $D_{VBI}$, no greater than 5 $D_{VBI}$, or no greater than 2 $D_{VBI}$.

Embodiment 40

The valve of any one of the preceding embodiments, wherein the valve comprises:
a first seal disposed between the valve stem and the valve body at a location between the at least one opening and a second longitudinal end of the valve stem; and
a second seal disposed between the valve stem and the valve body at a location between the first longitudinal end of the valve stem and the at least one opening.

Embodiment 41

The valve of embodiment 40, wherein fluid flow between the valve stem and valve body is prevented by the first seal when the valve is in the open and closed configurations.

Embodiment 42

The valve of any one of the preceding embodiments, wherein the valve is installable in a fluid system between a first fluid conduit and a second fluid conduit, wherein a first longitudinal end of the valve body is disposed closer to the first fluid conduit, and wherein fluid flow between the first and second fluid conduits passes directly between the second fluid conduit and the lumen of the valve stem through an opening in the second longitudinal end of the valve stem and directly between the lumen and the first fluid conduit through the at least one opening.

Embodiment 43

The valve of any one of the preceding embodiments, wherein the valve stem defines a barbed interface adjacent to the second longitudinal end adapted to receive a fluid conduit.

Embodiment 44

The valve of any one of the preceding embodiments, wherein the valve body is adapted to be coupled with a fluid conduit.

Embodiment 45

The valve of embodiment 44, wherein the valve body is adapted to be welded to the fluid conduit.

Embodiment 46

The valve of any one of embodiments 44 and 45, wherein the valve body is adapted to be sonically welded to the fluid conduit.

Embodiment 47

The valve of any one of the preceding embodiments, wherein the valve body comprises a flange disposed at a first longitudinal end thereof.

Embodiment 48

An assembly comprising:
a fluid reservoir;
a valve adapted to restrict fluid flow relative to the fluid reservoir, the valve comprising:
a valve body; and
a valve stem disposed at least partially within the valve body, the valve stem comprising a sidewall defining a central lumen and at least one opening in the sidewall,
wherein the valve is translatable between open and closed configurations, and wherein in the open configuration fluid flow passes directly between the lumen and the fluid reservoir through the at least one opening.

Embodiment 49

The assembly of embodiment 48, wherein the fluid reservoir comprises a bag adapted to contain a biologically active or pharmaceutical composition.

Embodiment 50

A method of operating a valve comprising:
removing a retention feature disposed between a first stop feature and a locking flange of a valve stem;
translating the valve stem in a longitudinal direction; and
installing the retention feature between a second locking feature of the valve stem and the locking flange.

Embodiment 51

The method of embodiment 50, wherein installing the retention feature is performed such that the valve stem remains at a fixed longitudinal position.

Embodiment 52

The method of any one of embodiments 50 and 51, wherein installing the retention feature is performed by translating the retention feature in a direction toward the valve stem.

Embodiment 53

The method of any one of embodiments 50-52, wherein installing the retention feature is performed by translating the retention feature perpendicular, or generally perpendicular, with a length of the valve stem.

Embodiment 54

The method of any one of embodiments 50-53, wherein removing the retention feature comprises disengaging the retention feature from the valve stem and a valve body containing at least a portion of the valve stem.

Embodiment 55

The method of any one of embodiments 50-53, wherein removing the retention feature comprises pulling the retention feature in a direction generally away from the valve stem.

Embodiment 56

The method of any one of embodiments 50-55, wherein the retention feature is adapted to maintain contact with the valve when disengaged therefrom.

Embodiment 57

The method of any one of embodiments 50-55, wherein the retention feature is adapted to be removed entirely from the valve when disengaged therefrom.

Embodiment 58

The method of any one of embodiments 50-57, wherein translating the valve stem to an open configuration requires an opening force, $F_O$, approximately equal to a closing force, $F_C$, required to translate the valve stem to a closed configuration, as measured when the fluid pressures on both sides of the valve are approximately equal.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

The invention claimed is:

1. A valve comprising:
   a valve body; and
   a valve stem disposed at least partially within the valve body, the valve stem comprising a sidewall defining a central lumen and at least one opening in the sidewall, wherein the valve is adapted to prevent fluid flow through the lumen when the at least one opening is disposed within the valve body and permit fluid flow through the lumen when the at least one opening is exposed from the valve body, and wherein the valve is essentially free of a spring; and
   a retention feature adapted to be installed within an aperture of the valve body, wherein the retention feature is detachable from the valve stem, wherein the valve stem defines at least one of a locking flange or a portion of the valve stem extending from the sidewall, and wherein at least one of the locking flange or the portion of the valve stem is adapted to engage with the retention feature to selectively maintain the valve stem in an open and closed configuration.

2. The valve of claim 1, wherein the valve is adapted to selectively restrict fluid flow relative to a bag containing a biologically active or pharmaceutical composition.

3. The valve of claim 1, wherein the valve body defines a first stop feature and a second stop feature spaced apart by an adjustment length, and wherein the locking flange is translatable along the adjustment length.

4. The valve of claim 3, wherein the adjustment length, $L_A$, is no less than a shortest distance, $D_O$, between a first longitudinal end of the valve stem and the at least one opening.

5. The valve of claim 4, wherein the locking flange is adapted to contact the first stop feature when the valve is in the open configuration and contact the second stop feature when the valve is in the closed configuration.

6. The valve of claim 4, wherein the retention feature is installable between the first and second stop features.

7. The valve of claim 4, wherein the retention feature is adapted to contact the second stop feature when the valve is in the open configuration and contact the first stop feature when the valve is in the closed configuration.

8. The valve of claim 4, wherein the retention feature is moveable between an engaged position and a disengaged position.

9. The valve of claim 1, wherein the valve stem is translatable within the valve body, and wherein an opening force, $F_O$, required to move the valve stem to an open configuration, is approximately equal to a closing force, $F_C$, required to move the valve stem to a closed configuration, as measured when fluid pressures on both longitudinal ends of the valve stem are approximately equal.

10. The valve of claim 1, wherein a first longitudinal end of the central lumen of the valve stem is closed.

11. The valve of claim 1, wherein the at least one opening comprises a plurality of openings.

12. The valve of claim 1, wherein a planar surface disposed on a first longitudinal end of the valve stem is tangent with the at least one opening.

13. The valve of claim 1, wherein the at least one opening is adapted to extend at least partially past a first longitudinal end of the valve body when the valve is in the open configuration.

14. The valve of claim 1, wherein the at least one opening is adapted to be disposed between first and second longitudinal ends of the valve body when the valve is in the closed configuration.

15. The valve of claim 1, wherein the valve comprises:
- a first seal disposed between the valve stem and the valve body at a location between the at least one opening and a second longitudinal end of the valve stem; and
- a second seal disposed between the valve stem and the valve body at a location between the first longitudinal end of the valve stem and the at least one opening.

16. The valve of claim 1, wherein the valve stem defines a barbed interface adjacent to a second longitudinal end adapted to receive a fluid conduit.

17. The valve of claim 1, wherein the valve body is adapted to be coupled with a fluid conduit.

18. The valve of claim 1, wherein the valve body comprises a flange disposed at a first longitudinal end thereof.

19. The valve of claim 1, wherein the locking flange is visible from a location external to the valve body.

\* \* \* \* \*